US008298543B2

(12) United States Patent
Brown-Driver et al.

(10) Patent No.: US 8,298,543 B2
(45) Date of Patent: *Oct. 30, 2012

(54) IDENTIFICATION AND APPLICATION OF ANTIBIOTIC SYNERGY

(75) Inventors: Vickie Brown-Driver, Solana Beach, CA (US); Kedar GC, San Diego, CA (US); John M. Finn, Encinitas, CA (US); Robert Haselbeck, San Diego, CA (US); Mark Hilgers, San Diego, CA (US); Karen Shaw, Poway, CA (US); Mark Stidham, San Diego, CA (US)

(73) Assignee: Trius Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/102,856

(22) Filed: May 6, 2011

(65) Prior Publication Data
US 2011/0294774 A1    Dec. 1, 2011

Related U.S. Application Data

(63) Continuation of application No. 11/636,379, filed on Dec. 8, 2006, now Pat. No. 8,021,665.

(60) Provisional application No. 60/751,245, filed on Dec. 16, 2005, provisional application No. 60/749,299, filed on Dec. 9, 2005.

(51) Int. Cl.
*A61K 31/00*     (2006.01)
*A61K 31/43*     (2006.01)
*A61K 39/00*     (2006.01)

(52) U.S. Cl. .......... 424/184.1; 514/1; 514/198; 514/199
(58) Field of Classification Search .................. None
See application file for complete search history.

(56) References Cited

U.S. PATENT DOCUMENTS

| 4,751,295 A * | 6/1988 | Oka et al. ............... 540/222 |
| 6,436,933 B1 | 8/2002 | Rideout et al. |
| 8,021,665 B2 * | 9/2011 | Brown-Driver et al. ... 424/184.1 |

FOREIGN PATENT DOCUMENTS

| JP | 11-221085 A | 8/1999 |
| JP | 11-235178 A | 8/1999 |

OTHER PUBLICATIONS

Zurabyan et al (Antibiotiki I Khimioterapiya vol. 39 (9-10), pp. 40-44, 1994).*
Andres et al (Bioorganic & Medicinal Chemistry Letters vol. 10, pp. 715-717, 2000).*
Barakett et al., "Synergy of cefotaxime and fosfomycin against penicillin-resistant pneumococci", *J. Antimicrob. Chemother.*, 31(1): 105-109 (1993).
Berger-Bachi et al., "Factors influencing methicillin resistance in staphylococci", *Arch. Microbiol.*, 178:165-171 (2002).
Beyer et al., "New class of bacterial phenylalanyl-tRNA synthetase inhibitors with high potency and broad-spectrum activity", *Antimicrob. Agents Chemother.*, 48(2):525-532 (2004).
Blacky et al., "In vitro activity of fosfomycin alone and in combination with amoxicillin, clarithromycin and metronidazole against *Helicobacter pylori* compared with combined clarithromycin and metronidazole", *Eur. J. Clin. Microbiol. Infect. Dis.*, 24(4):276-279 (2005).
Chin et al., "Synergy of fosfomycin with beta-lactam antibiotics against staphylococci and aerobic gram-negative bacilli", *Drugs Exp. Clin. Res.*, 12(12):943-947 (1986).
Coyle et al., "Influences of linezolid, penicillin, and clindamycin, alone and in combination, on streptococcal pyrogenic exotoxin a release", *Antimicrob. Agents Chemother.*, 47(5):1752-175 (2003).
Dryselius et al., "Antimicrobial synergy between mRNA- and protein-level inhibitors", *Journal of Antimicrobial Chemotherapy*, 56:97-103 (2005).
Dulaney et al., "Synergy between fosfomycin and arenaemycin", *J. Antibiol.*, 41(7):982-983 No abstract available. 1988.
Figueredo et al., "Synergy of ciprofloxacin with fosfomycin in vitro against *Pseudomonas* isolates from patients with cystic fibrosis", *J. Antimicrob. Chemother.*, 22(1):41-50 (1988).
Forsyth et al., "A genome-wide strategy for the identification of essential genes in *Staphylococcus aureus*", *Mol. Microbiol.*, 42(6): 1387-400, 2002.
Fosse et al., "In vitro study of the cefamandole-fosfomycin combination against methicillin-resistant staphylococci", *Pathol. Biol.*, 32(5 PI2):528-531 (1984).
Gardete et al., "Role of murE in the Expression of p-Lactam Antibiotic Resistance in *Staphylococcus aureus*", *Journal of Bacteriology*, 186(6): 1705-1713 (2004).
Gardete et al., "Role of murE in the Expression of beta-lactam antibiotic resistance in *Staphylococcus aureus*", *J. Bacteriol.*, 186(6): 1705-1713 (2004).

(Continued)

*Primary Examiner* — Albert Navarro
(74) *Attorney, Agent, or Firm* — DLA Piper LLP (US)

(57) ABSTRACT

The present invention provides a pharmaceutical composition useful for treating bacterial infections in humans and animals which comprises administering to a human or animal in need thereof, an antibacterially effective combination of a β-lactam antibiotic and an inhibitor of any bacterial peptidoglycan biosynthesis enzyme, especially GlmU, GlmU, MurA, MurB, MurC, MurD, MurE, MurF, MurG, MraY, and UppS. Further provided is a method of discovering synergists for antibiotics including: a) expressing in a cell an antisense nucleic acid against a nucleic acid encoding a gene product so as to reduce the activity or amount of the gene product in the cell, thereby producing a cell sensitized to an antibiotic; b) characterizing the sensitization of the cell to the antibiotic and selecting pairs of antibiotics and genes that result in antibiotic efficacy at one-fifth or less the concentration required in the absence of the antisense gene; c) screening for chemical compounds that inhibit the gene product corresponding to the selected synergistic gene; and d) selecting or creating chemical analogs that inhibit the gene product corresponding to the selected synergistic gene such that the inhibition occurs in the bacteria.

10 Claims, 9 Drawing Sheets

OTHER PUBLICATIONS

Grif et al., "In vitro activity of fosfomycin in combination with various antistaphylococcal substances", *J. Antimicrob. Chemother.*, 48(2):209-217 (2001).

Grossato et al., "Effect of non-beta-lactam antibiotics on penicillin-binding protein synthesis of *Enterococcus hirae* ATCC 9790", *J. Antimicrob. Chemother.*, 27(3):263-271 (1991).

Haller I., "Comprehensive evaluation of ciprofloxacin in combination with beta-lactam antibiotics against *Enterobacteriaceae* and *Pseudomonas aeruginosa*", *Arzneimittelforschung*, 36(2):226-229 (1986).

Hamilton-Miller et al., "In vitro activity of fosfomycin against 'problem' gram-positive cocci", Microbios, 71(287):95-103 (1992).

Ji et al., "Identification of essential genes in *Staphylococcus aureus* using inducible antisense RNA", Methods Enzymol., 358:123-128 (2002).

Kedar et al., "Evaluation of the *metS* and *murB* Loci for Antibiotic Discovery Using Targeted Antisense RNA Expression Analysis in *Bacillus anthracis*", *Antimicrobial Agents and Chemotherapy*, 51(5):1708-1718 (2007).

Kikuchi et al., "Effects of combination of benzylpenicillin and fosfomycin on penicillin-resistant *Streptococcus pneumoniae*", *Microb. Drug Resist.*, (2): 185-189 (1995).

Marcolongo et al., "An intravenous penicillin-erythromycin lactobionate combination in the treatment of bacterial endocarditis caused by enterococcus", *Minerva Cardioangiol.*, 35(4):193-194 (1987).

Montefiore et al., "Pyogenic meningitis in Ibadan, Nigeria. A 15-month prospective study", *Scand. J. Infect. Dis.*, 10(2):113-117 (1978).

Mory et al., "In vitro activities of cefotaxime, vancomycin, quinupristin/dalfopristin, linezolid and other antibiotics alone and in combination against *Propionibacterium acnes* isolates from central nervous systems infections", J. Antimicrob. Chemother., 55(2):265-268 (2005).

Neu et al., "In vitro activity of fleroxacin in combination with other antimicrobial agents", *Am. J. Med.*, 94(3A):9S-16S. Review (1993).

Sieradzki et al., "Suppression of beta-lactam antibiotic resistance in a methicillin-resistant *Staphylococcus aureus* through synergic action of early cell wall inhibitors and some other antibiotics", *J. Antimicrob. Chemother.*, 39(Suppl A):47-51 (1997).

Sobral et al., "Normally functioning murF is essential for the optimal expression of methicillin resistance in *Staphylococcus aureus*", *Microb. Drug Resist.*, 9(3):231-241 (2003).

Tessieretal., "In vitro activity of fosfomycin combined with ceftazidime, imipenem, amikacin, and ciprofloxacin against *Pseudomonas aeruginosa*", *Eur. J. Clin. Microbiol. Infect. Dis.*, 16(2): 159-162 (1997).

Utsui et al., "Antibacterial activity of cefmetazole alone and in combination with fosfomycin against methicillin- and cephem-resistant *Staphylococcus aureus*", *Antimicrob. Agents Chemother.*, 30(6):917-922 (1986).

Vincent et al., "Infectious exanthems and unusual infections", Adolesc. Med., 11(2):327-58 (2000).

Yin et al., "Identification of antimicrobial targets using a comprehensive genomic approach", *Pharmacogenomics*, 5(1):101-113 (2004).

Alvarez et al., "In vitro activity of fosfomycin, alone and in combination, against methicillin-resistant *Staphylococcus aureus*", *Antimicrob. Agents Chemother.*, 28(5):689-690 (1985).

Bronson et al., "Discovery of the first antibacterial small molecule inhibitors of MurB", *Bioorg. Med. Chem. Lett.*, 13(5):873-875 (2003).

Francisco et al., "Phenyl thiazolyl urea and carbamate derivatives as new inhibitors of bacterial cell-wall biosynthesis", *Bioorg. Med. Chem. Lett.*, Jan. 5, 2004; 14(1):235-238 (2004).

Kutterer et al., "4-Alkyl and 4,4'-dialkyl 1,2-bis(4-chlorophenyl)pyrazolidine-3,5-dione derivatives as new inhibitors of bacterial cell wall biosynthesis", *Bioorg. Med. Chem. Lett.*, 15(10):2527-2531 (2005).

Li et al., "2-Phenyl-5,6-dihydro-2H-thieno[3,2-c]pyrazol-3-ol derivatives as new inhibitors of bacterial cell wall biosynthesis", *Bioorg. Med. Chem. Lett.*, 13(15):2591-2594 (2003).

McCoy et al., "In vitro and in vivo functional activity of *Chlamydia* MurA, a UDP-N-acetylglucosamine enolpyruvyl transferase involved in peptidoglycan synthesis and fosfomycin resistance", *J. Bacteriol.*, 185(4):1218-1228 (2003).

Saionji et al., "Antibacterial activities and electron microscopic studies of imipenem in combination with fosfomycin against methicillin and fosfomycin resistant strains of *Staphylococcus aureus*", *Jpn. J. Antibiot.*, 43(3):379-387 (1990). Abstract Only.

\* cited by examiner

Figure 1. Biosynthetic pathway of the peptidoglycan monomer unit in bacteria.

Figure 3. *B. anthracis* murB-2 antisense strain sensitivity to (a) cephalosporins and (b) other antibiotics, including beta-lactams cloxacillin, oxacillin, and dicloxacillin.

Figure 4. *B. anthracis murA1* antisense strains sensitivity to various antibiotics.

**Synergy between Cefotaxime and murB2 compounds on *Bacillus anthracis***

| | Growth |
|---|---|
| | No Growth |

• Wt *B. anthracis* in MIC format with checkerboard compound concentration

• Cefotaxime MIC ≥8ug/ml
• Rx106 MIC >128
• Rx107 MIC 4-8 ug/ml

| | MIC | combo | FIC | FICI |
|---|---|---|---|---|
| Cefotaxime | 8 | 1 | 0.125 | 0.19 |
| Rx000106 | 128 | 8 | 0.0625 | |

| | MIC | combo | FIC | FICI |
|---|---|---|---|---|
| Cefotaxime | 8 | 0.125 | 0.015625 | 0.27 |
| Rx000107 | 4 | 1 | 0.25 | |

Fig. 6. *S. aureus* engineered with *murB* antisense
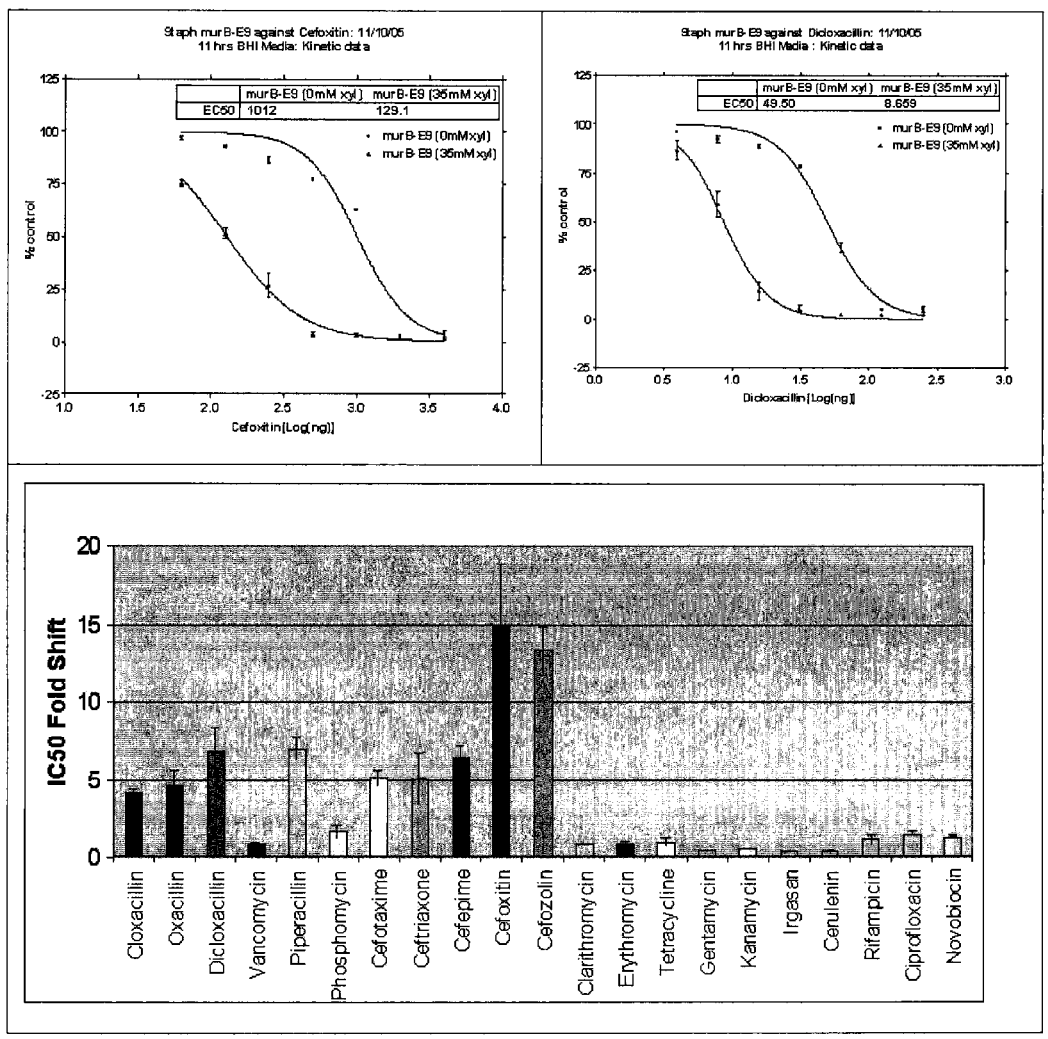

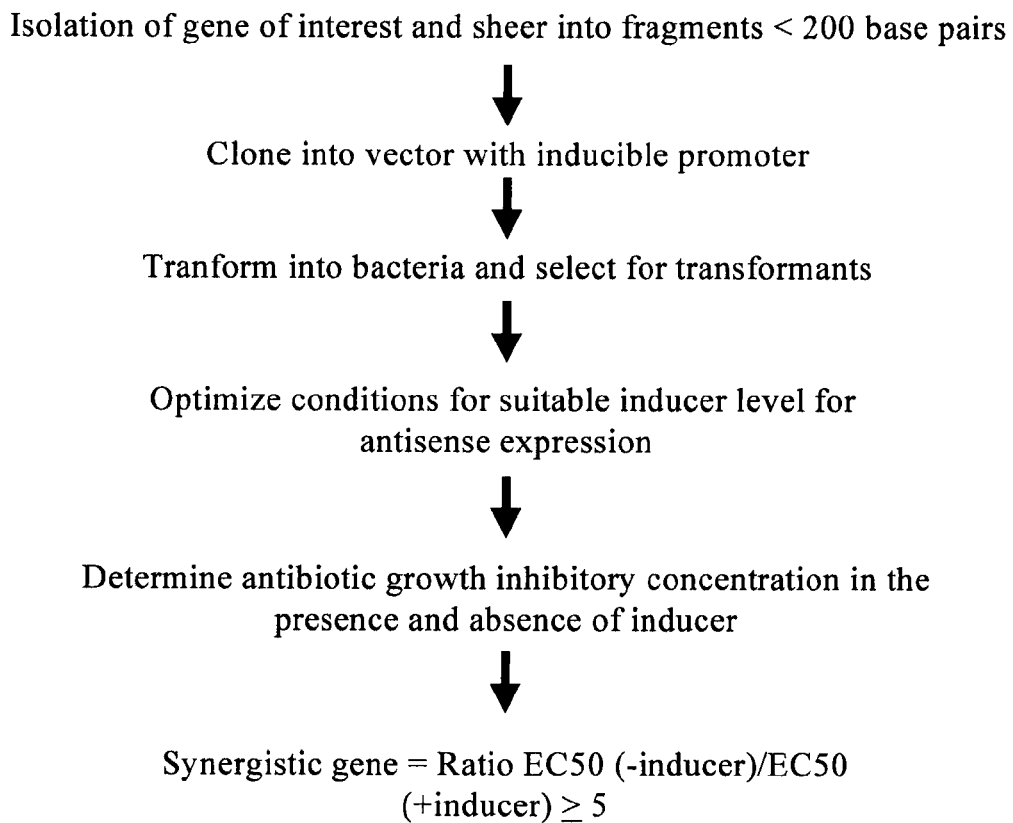
Figure 7. Process for the discovery of synergistic targets and synergists

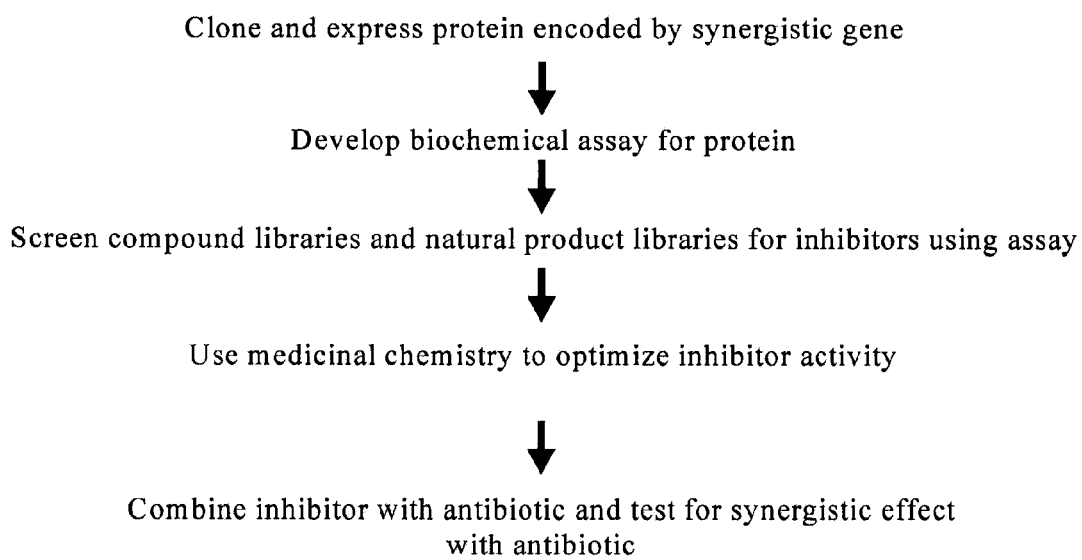

Figure 7 (Cont.) Process for the discovery of synergistic targets and synergists Clone and express protein encoded by synergistic gene
↓
Develop biochemical assay for protein
↓
Screen compound libraries and natural product libraries for inhibitors using assay
↓
Use medicinal chemistry to optimize inhibitor activity
↓
Combine inhibitor with antibiotic and test for synergistic effect with antibiotic

Figure 8.

| SEQ ID | SOURCE ORGANISM | SEQUENCE |
|---|---|---|
| Ba-murB2-C1 | Bacillus anthracis | CCGCCAACTGAACCTGGAATACCACAAGCGAACTCAAGACCCGTTAAGTTATGGTCTAACGCAATACG TGATACGTCAATAATTGCTGCACCGCACTGTGCTACAATTGTCGT |
| Ba-murB2-H1 | Bacillus anthracis | CTCTTCAACTGTTTTTTGTACGAAGTGAATTAAATCGATGTAATCTTGTGCTGTTCCGTTATCAACATTT ACCATAAATCCAGCGTGTTTTAAAGAAACGGATCGAATGTCATTATTAAAGACG |
| Ba-murB2-D1 | Bacillus anthracis | TGCATTCATATATAATGCTCCGCCAACTGAACCTGGAATACCACAAGCGAACTCAAGACCCGTTAAGT TATGGTCTAACGCAATACGTGATACGTCAATAATTGCTGCACCGCACTGTGCTACAATTGTCGTTCCT GTTACAGTAACACCTGTAATATGAATTAAACTTACTGT |
| Ba-murB2-D2 | Bacillus anthracis | AAGTTATGGTCTAACGCAATACGTGATACGTCAATAATTGCTGCACCGCACTGTGCTACAATTGTCGT TCCTGTTACAGTAACACCTGTAATATGAATTAAACTTACTGTAATCCCGCGAATTCCACCGTCTTTAAT AATGACAT |
| Ba-metRS1-H1 | Bacillus anthracis | AATATAACTGGATCTACTACATTTCCTTTTGACTTACTCATCTTTCCATCCTTCATTAAAATCCAACCGT GAGCAAAGACTTTTTTCGGAAGAGGT |
| Ba-metRS1-H2 | Bacillus anthracis | AACTTATCTGCCTTTTTTACAGGTTCAGCAGATAGTACTTCAGCTACACGCAATTCTACTTTAAAGAAA TCATCAATTGTAATTTCTTCTGCCTTCGGTCCTTCTTC |
| Ba-metRS1-H6 | Bacillus anthracis | ATCCTTCATTAAAATCCAACCGTGAGCAAAGACTTTTTTCGGAAGAGGTAAATCTAATGCCATTAAAAT GATTGGCCAATAAATTGTATGGAAACGAACGATT |
| Ba-metRS1-E4 | Bacillus anthracis | GGTTGTCCTTTTTCTACTTTTGTTCCAGCTGGAATACAGCCGATTGTAGATAGGCTTCCCCAAGATGT ATGTGCTTCATCAGTAAGGCCAAGC |
| Ba-uppS-UG9 | Bacillus anthracis | TTTAACGCGAAATTAAGAATTAATCCCGTATTCTCTTTCGTTTCTTCCATGGCCTTCTCCATCGCTCTG CGTGTATGCGTAGGAAGACGATCTTGTTGC |
| Ba-uppS-UA3 | Bacillus anthracis | CCTCTCTTTCTACACGCCTCCGAATCTGCGCCCTCTATGTTGAAAGTCTGT |
| Ba-dfrA-2G1 | Bacillus anthracis | CCAGGCAGTGGTCTACCAATCGCTTCATAGTTTTTTCTTCCCATAATAAGCGGGTGACCCATCGTTGT TTTCTTTACATACTGCAATTCACTCGGTAAACGCC |
| Ba-dfrA-2G6 | Bacillus anthracis | CAGGCAGTGGTCTACCAATCGCTTCATAGTTTTTTCTTCCCATAATAAGCGGGTGACCCATCGTTGTT TTCTTTACATACTGCAATTCACTCGGTAAACGCCAAGGT |
| Sa-murB-E9 | Staphylococcus aureus | CCACCTTCACGGATAATAATATTTGAGCCATTTCCTAAATATGTAACAGGAATCTCATTTTGATAGGCA TATTTAACAACTGCTTGTACTTCTTCATTTTTAGTAGGGGTAATGTAAAAGTCGGCATTACCACCTGTT TTAGTATAAGTGTATCGTTTTAAAGGTTCATCAACTTTAATTTTTTCATTTGGGATAAGT |
| Sa-murB-F7 | Staphylococcus aureus | CTTGCAAATTAGAATCTTGTATCAATTTACCTGCAAAATGACCAGGCGGTCTTTGGAATACACTACCAC ATGAAGGATACTCTAAAGGTTGTTTAGATTCTCTACGTTCTGTTAAATCATCCATTTTAGCTTGTATTTC AGTCATTTTACCAGGAGCTAAAGTAAATGC |
| Sa-murB-B9 | Staphylococcus aureus | ACCAATTGAACCTGGAATACCACATGCAAATTCAAGGCCAGTAAGTGCGTAATCACGAGCAACACGTG AGACATCAATAATTGCAGCGCCGCTACCGGCTATTATCGCATCATCAGATACTTCGATATGATCTAGT GATAATAAAC |

IDENTIFICATION AND APPLICATION OF ANTIBIOTIC SYNERGY

RELATED APPLICATIONS

This is a continuation of U.S. patent application Ser. No. 11/636,379, filed Dec. 8, 2006 now U.S. Pat. No. 8,021,665, which claims priority under §35 U.S.C. §119(e) from U.S. Provisional Patent Application Ser. Nos. 60/751,245 filed Dec. 16, 2005 and 60/749,299 filed Dec. 9, 2005, each of which are hereby incorporated by reference in their entirety for all purposes.

BACKGROUND OF THE INVENTION

1. Field of the Invention

This invention relates generally to bacterial diseases and more specifically to combinations of compounds that enable therapeutic control of bacterial infections at doses of the compounds much lower than either of the compounds administered alone, especially inhibitors of MurB in combination with β-lactam antibiotics.

2. Background Information

The few available distinct classes of antimicrobial compounds limit the scope for single and combination drug treatment of bacterial infections, including infections involving antibiotic-resistant bacteria. Antibacterial chemotherapy research has therefore focused on the discovery of novel targets for new antibacterial development. An alternative approach to the discovery of new antibacterial compounds is the discovery of antibiotic synergists. Synergism in antimicrobial therapy is well known and is used to describe supra-additive activity of antibiotics used in combinations. For example, in the treatment of bacterial infections combinations such as penicillin or ampicillin and streptomycin or gentamycin have been shown to have a supra-additive effect against enterococci infections. Similarly, carbenicillin or ticarcillin combined with an aminoglycoside such as gentamycin or tobramycin exhibit a synergistic effect in the treatment of *Pseudomonas aeruginosa* infection. Combined therapy using streptomycin together with tetracycline is more effective in the therapy of brucellosis than either agent alone, and a mixture of chloramphenicol plus a sulfonamide is more effective against meningitis due to *Haemophilus influenzae*.

One method, which is used to predict the efficacy of antibacterial agents is described by Scribner et. al., (1982, Antimicrobial Agents and Chemotherapy 21(6):939-943) and in Goodman & Gilman (1980, The Pharmacological Basis of Therapeutics, Sixth Edition, pp. 1097-1098) and is referred to as the checkerboard assay. This assay involves serial two-fold dilutions of the antibiotics individually and in combination in broth, which is then inoculated with the microorganism to be tested. After incubation, the minimum inhibitory concentration (MIC) of each drug used individually and in combination is determined (N.B., the MIC is the lowest concentration of the drug that inhibits growth in the medium). Synergism is indicated by a decrease in the MIC of each drug when used in combination. Antagonism is indicated by an increase in the MIC of either or both drugs when used in combination.

In the above examples, synergism is discovered through the empirical testing of pairs of antibiotics. Synergists may also include compounds that inhibit pathogens capacity to inactivate the antibiotic through metabolic detoxification, compounds that inhibit cellular pumps that export the antibiotic, and compounds that otherwise decrease the minimal inhibitory concentration (MIC) of the antibiotic. Development of a combination containing Amoxycillin and Clavulanic acid is the best example to illustrate such efforts. Amoxycillin is an amino-penicillin and is degraded by beta-lactamase producing bacteria. Clavulanic acid was discovered to inhibit the activity of beta-lactamase but is devoid of antibacterial activity of its own (Reading C & Cole M, 1977. A beta lactamase inhibiting beta-lactam from *Streptomyces clavuligenus*; Antimicrob Agents Chemother, 11, p-852-857; Reading C, Farmer T & Cole, M 1983, The Beta lactamase stability of Amoxycillin with beta lactamase inhibiting Clavulanic acid, J. Antimicrob Chemother., 11, p-27-32; Todd P A & Benfield P 1990. Amoxycillin/Clavulanic acid, an update of its antibacterial activity, pharmacokinetic properties & Therapeutic use, Drugs 39, p-264-307).

In the case of clavulanic acid, the importance of beta-lactamases in imparting resistance to beta-lactam antibiotics was well understood. This understanding allowed targeted development of beta-lactamase inhibitors.

There may be other processes important in limiting the effectiveness of any particular antibiotic. An understanding of the different processes can result in the identification of targets for synergist development much like the case of clavulanic acid. Therefore, it would be useful to have a general way of finding processes that limit antibiotic activity so that targeted synergist development could occur.

Bacterial cell wall biosynthesis is an essential process in bacteria in which peptidoglycans are produced inside the bacteria, transported to the outer membrane, and cross-linked together to form the cell wall. Important therapeutic antibiotics, including penicillins and cephalosporins, inhibit the cross-linking process catalyzed by penicillin-binding proteins. FIG. 1 is a diagram of the process. Of particular interest is the step catalyzed by the MurA enzyme (also known as UDP-N-acetylglucosamine enolpyruvyl transferase, EC 2.5.1.7), which is encoded by murA gene and inhibited by fosfomycin. Also of interest is the next step catalyzed by the MurB enzyme and encoded by the murB gene UDP-N-acetylenolpyruvylglucosamine reductase, EC 1.1.1.158).

The process occurring outside the cell membrane, (transglycosylation and transpeptdation) cross-links peptidoglycan monomers. These reactions are catalyzed by penicillin-binding proteins (PBPs), which are the target sites of the penicillin and cephalosporin antibiotics. There are multiple PBPs in bacteria, each species having its own assortment. The PBPs occur in a small number of copies per cell, from a few hundred to one or two thousand and include low-molecular weight (low-Mr) PBPs, high-Mr PBPs, and β-lactamases. All three classes have active-site serine residues important in their catalytic function. Penicillin and cephalosporins act as suicide substrates that inactivate PBPs, thus inhibiting the final steps of cell wall biosynthesis. β-lactamases are structurally related to the PBPs with active-site serines that act on penicillins and cephalosporins. However, in the case of the β-lactamases, the interaction with the penicillin or cephalosporin results in the hydrolysis of the antibiotic, ruining their ability to interact with PBPs.

There are many studies in the literature concerning the combination of fosfomycin with cephalosporins and penicillins. Alvarez et al. (1985) reported synergism was observed in 66% of strains with fosfomycin-cefamandole and in 46% of strains with fosfomycin-methicillin. The synergy reported in this study was defined if the minimum inhibitory concentrations (MICs) of both drugs decreased by one-fourth. Utsui et al (1986) reported on in vitro and in vivo antibacterial activities of cefinetazole and cefotaxime alone and in combination with fosfomycin against methicillin- and cephem-resistant strains of *Staphylococcus aureus*. This study showed the one-fourth reduction in MIC for both drugs as a measure of synergy. This study also demonstrated accelerated killing of bacteria in the combination treatments, another form of synergy.

The study of Utsui et al. included detection of fosfomycin-induced specific PBP profiles.

The levels of several of the PBPs were reduced significantly upon exposure to fosfomycin. Since cephalosporins act by inactivating PBPs, the researchers concluded a reduction in PBPs would make the cephalosporins more effective by reducing the number target proteins to inhibit. They further speculated that peptidoglycan monomers are inducers of PBP transcription. Inhibition of peptidoglycan biosynthesis by fosfomycin would reduce the levels of peptidoglycan, thus inhibiting transcription of PBPs.

Genetic studies on the interaction of peptidoglycan biosynthesis enzymes and beta-lactamase inhibitors demonstrate that interference in murE or murF in methicillin-resistant *Staphylococcus aureus* have increased sensitivity to the beta-lactam oxacillin (Sieradzki et al., 1997; Sobral et al., 2003; Gardete et al., 2004). The implications of these studies are that MurE and MurF activity is necessary for the expression of beta-lactam resistance. It is therefore logical that inhibitors of MurE or MurF could also increase the sensitivity of methicillin-resistant *S. aureus* to oxacillin and other beta-lactam antibiotics.

None of these studies anticipate that a chemical inhibitor of peptidoglycan biosynthesis enzymes would increase the sensitivity of non-resistant bacteria to beta lactam antibiotics.

Antisense has been useful in identifying targets in bacteria for new antibiotics. There are many publications demonstrating the use of antisense to discover such targets and to use the antisense clones as sensitized cells to detect inhibitors of the antisense target.

The concept behind these inventions are (1) antisense expression can differentiate genes that are specifically related to 'essential' to bacteria, thus defining a set of targets for use in antibiotic discovery and (2) antisense expression can result in cells sensitized to compounds specifically inhibiting the protein corresponding to the mRNA targeted by the antisense. This latter use of antisense can result in the use of sensitized cells in finding target-specific inhibitors from a chemical library or a natural product collection.

None of these references describe the use of antisense to identify targets for synergist discovery.

Useful synergistic combinations of antibiotics can be discovered through systematic testing of pairs of antibiotics, through targeted research for compounds that decrease antibiotic metabolism by the pathogen, or through random or rational screening of chemical entities or extracts with specific antibiotics.

Antisense has been used to discover essential genes and to develop tools for discovery of novel antibiotic compounds.

SUMMARY OF THE INVENTION

In general, the present invention provides a method of discovering synergistic genes for antibiotics, comprising the steps of:
a. expressing in a cell an antisense nucleic acid against a nucleic acid encoding a gene product so as to reduce the activity or amount of the gene product in the cell, thereby producing a cell sensitized to an antibiotic; and
b. characterizing the sensitization of the cell to the antibiotic and selecting pairs of antibiotics and genes that result in antibiotic efficacy at one-fifth or less the concentration required in the absence of the antisense gene.

The present invention also provides a method of discovering synergists for antibiotics, comprising:
a. screening for chemical compounds that inhibit the gene product corresponding to the selected synergistic gene;
b. selecting or creating chemical analogs that inhibit the gene product corresponding to the selected synergistic gene such that the inhibition occurs in the bacterium; and
c. combining the synergistic inhibitor with the antibiotic and determining antimicrobial activity of the combination at various concentrations of each.

In one embodiment, the present invention provides a method of increasing the antibacterial potency of beta-lactam antibiotics, thus having utility in methods for preventing or treating bacterial infections in animals.

In another embodiment, the present invention comprises the combination of an inhibitor of MurB with a cell wall inhibiting antibiotic, especially a beta-lactam antibiotic.

An improved method for identifying microbial gene fragments that, when ectopically expressed in the antisense orientation, results in post-transcriptional inhibition of expression of a microbial gene of interest, thereby causing a phenotypic change in the microorganism that can be observed and measured. Once successfully identified, conditional expression of such antisense-oriented fragments can be used to lower the concentration of the specific gene product within the cell, thereby hypersensitizing the cell to second agents that are themselves specific inhibitors of the gene product. If the observed phenotype constitutes a loss of the ability to proliferate, then this hypersensitivity can be the basis of an assay to test the mechanism of action compounds with antimicrobial activity. Such an assay would be able to distinguish between antimicrobial compounds whose ability to cause loss of proliferation is linked to specific effects on a target gene product of interest, and those compound, and those for which there is no observed link. The improved method would speed development of such assays by definitively identifying the most suitable antisense DNA fragments.

Two earlier patents, U.S. Pat. No. 6,228,579 and U.S. Pat. No. 6,924,101, describe a process by which DNA fragments of microbial genomic DNA are surveyed for their ability to reduce or block proliferation when expressed in the microorganism in the antisense orientation. In brief, genomic DNA is fragmented, the fragments are cloned behind an inducible promoter on a plasmid, the plasmid is introduced into the microorganism of interest, and then proliferation is measured and compared in the presence and absence of an inducer compound or stimulus that results in a dependent presence or absence of expression of the cloned fragment.

Fragments can be cloned in relation to the promoter in either the sense or antisense orientation. If the fragment in the antisense orientation, there is an assumption that those fragments that cause reduction or blockage of proliferation of the microorganism do so by a mechanism that is specific to the function of the gene from which the fragment was derived, implying that this gene is one whose encoded cellular function is required for normal proliferation.

However, with the use of our improved method for identifying antisense fragments that lead to specific inhibition of target genes, we have shown that the statement above is not true. Indeed, we recognize that a fragment that is expressed from a promoter as described can reduce proliferation by a number of means that are NOT specific to the indicated gene and gene product. A fragment that is expressed in either the ostensible sense or antisense orientation can result in 1) an RNA species that can act as an aptamer or other kind of inhibitor to another unrelated function in the cell, 2) an RNA species that can be expressed in a reading frame other than that of the original gene to produce a peptide with unspecific toxic properties. For this reason, an antisense-based screen as described in the above patents could result in false positives, i.e., a gene that does not encode a function that is essential for proliferation could be identified as such, solely on the appearance in a screen of a growth inhibitory antisense fragment of that gene. This could lead to a miss-identification of the gene as essential for proliferation and as such, a likely antibiotic development target.

Focus on a gene or gene of interest rather than the entire genome of an organism. This allows a much greater representation of the gene or gene of interest in the screen for fragments that cause a target-specific phenotypic effect. Using whole genomic DNA to find antisense fragments to a specific gene or genes of interest results in longer screens Incorporation of validation steps in the discovery process for identifying which antisense fragments that cause a phenotypic change are doing so concomitant with specific reduction in intact mRNA expressed from the gene from which the antisense fragments are derived.

BRIEF DESCRIPTION OF FIGURES

FIG. 3(a) and (b) show B. anthracis murB-2 antisense strain sensitivity to (a) cephalosporins and (b) other antibiotics, including beta-lactams cloxacillin, oxacillin, and dicloxacillin.

FIG. 4 shows B. anthracis murA1 antisense strains sensitivity to various antibiotics.

FIG. 5 shows an FICI experiment in wild-type B. anthracis using cefotaxime and dihydropyrrolone MurB inhibitors Rx 000106 or Rx 000107. In the checkerboard experiment, the fractional inhibitory concentration (FIC) of a compound is computed as the ratio of the minimum inhibitory concentration (MIC) of the compound alone and in combination. The FIC Index (FICI) is the sum of the FIC for the two compounds.

FIG. 6 shows S. aureus engineered with murB antisense.

FIG. 7 shows a process for the discovery of synergistic targets and synergists.

FIG. 8 is a table of target sequences (SEQ ID NO'S 1 to 15).

DETAILED DESCRIPTION OF THE INVENTION

"Beta-lactam" A beta-lactam (β-lactam) is a lactam with a heteroatomic ring structure, consisting of three carbon atoms and one nitrogen atom. The beta-lactam ring is part of several antibiotics, such as penicillin, which are therefore also called beta-lactam antibiotics. These antibiotics work by inhibiting the bacterial cell wall synthesis. Examples of beta-lactam antibiotic classes include penicillins, cephalosporins, and cabapenems.

[Chemical structure of beta-lactam with substituents R1, R2, R3]

"Antibiotic" is a compound used to control infections. Examples of antibiotics include Cell Wall Inhibitors Beta-lactams (penicillin G, penicillin V, nafcillin, methicillin, oxacillin, cloxacillin, dicloxacillin, flucloxacillin, ampicillin, amoxacillin, carbenicillin, ticarcillin, azocillin, mezlocillin, pipericillin, Cephalosporins, cephalothin, cefazolin, cefalexin, cefuroxime, cefamandole, cefoxitin, cefaclor, moxalactam, cefaperazone, ceftazidime, ceftriaxone, clavulanic acid, sulbactam, imipenem, aztreonam, Cefoxitin, cefozolin, Cefaclor)

Inhibitors of peptidoglycan biosynthesis include but are not limited to:

1. Inhibitors of GlmU, MurA (Fosfomycin)
2. Inhibitors of MurB (dihydropyrrolones)
3. Inhibitors of Undecaprenyl pyrophosphate Synthetase (hydantoins, sulfonamides)
4. Inhibitors of LpxC (UDP-3-O-acyl N-acetylglycosamine deacetylase)

Lipopeptides (daptomycin)

Isoprenoid biosynthesis inhibitors (bacitracin, phosmidomycin)

Fatty acid biosynthesis inhibitors (cerulenin, triclosan, isoniazid)

Protein synthesis inhibitors 1. aminoglycosides (streptomycin, gentamicin and kanamycin),
2. tetracyclines
3. chloramphenicol,
4. macrolides (erythromycin, azithromycin, clarithromycin),
5. lincosamides (lincomycin and clindamycin), and
6. oxazolidinones (linezolid)

tRNA synthetase inhibitors such as mupirocin

1. MetRS inhibitors (catechols, prolines, quinolones)
2. Peptide deformylase inhibitors (hydroxamates)

RNA synthesis inhibitors such as rifampicin,

DNA gyrase inhibitors such as quinolones (nalidixic acid, ciprofloxacin)

Antifolates (trimethoprim and sulfamethoxazole)

"Synergism" is defined as a fractional inhibitory concentration index (FICI) of ≦0.5, where FICI is defined as the sum of the fractional inhibitory concentrations (FICs) of the individual components in a combination of two compounds, and the FIC is defined as the ratio of the minimal inhibitory concentration (MIC) of the compound in the combination divided by the MIC of the compound alone.

"Antisense Synergism" is defined as a ratio of the 50% Inhibitory Concentration (IC50) of a compound in the presence of an inducer divided by the IC50 in the absence of inducer ≧5.

Figure 1:
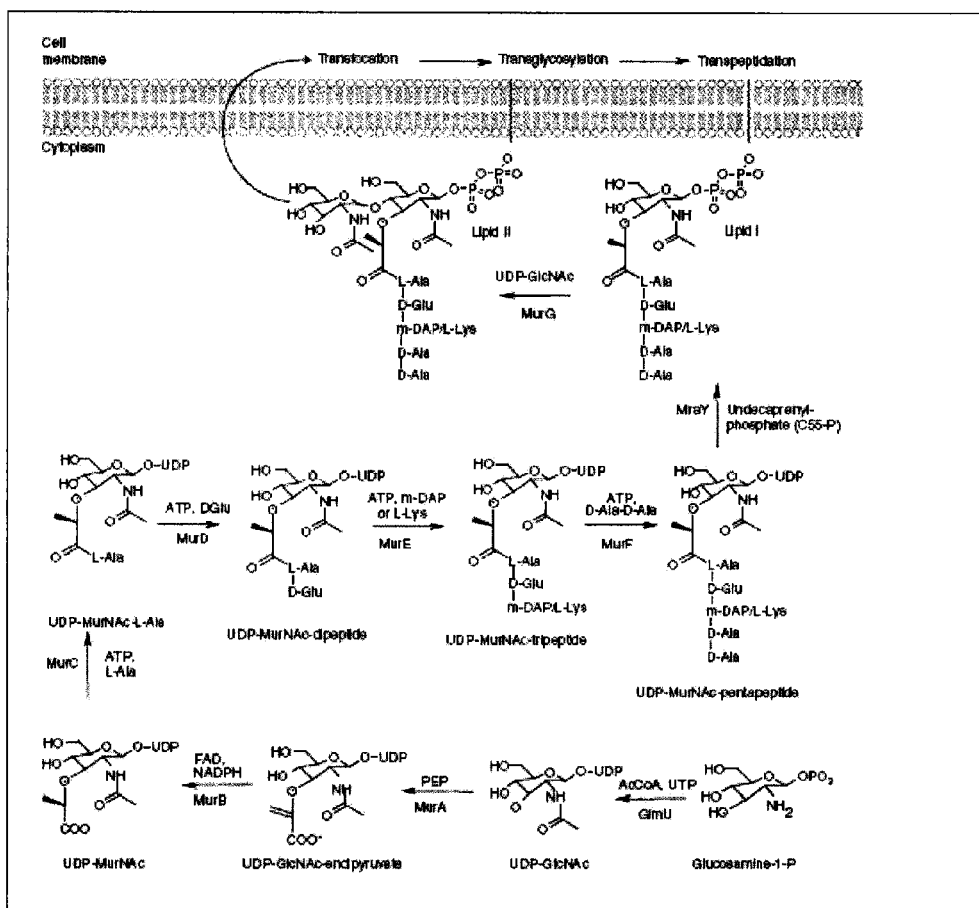
FIG. 1 shows a biosynthetic pathway of the peptidoglycan monomer unit in bacteria.
Figure 2:
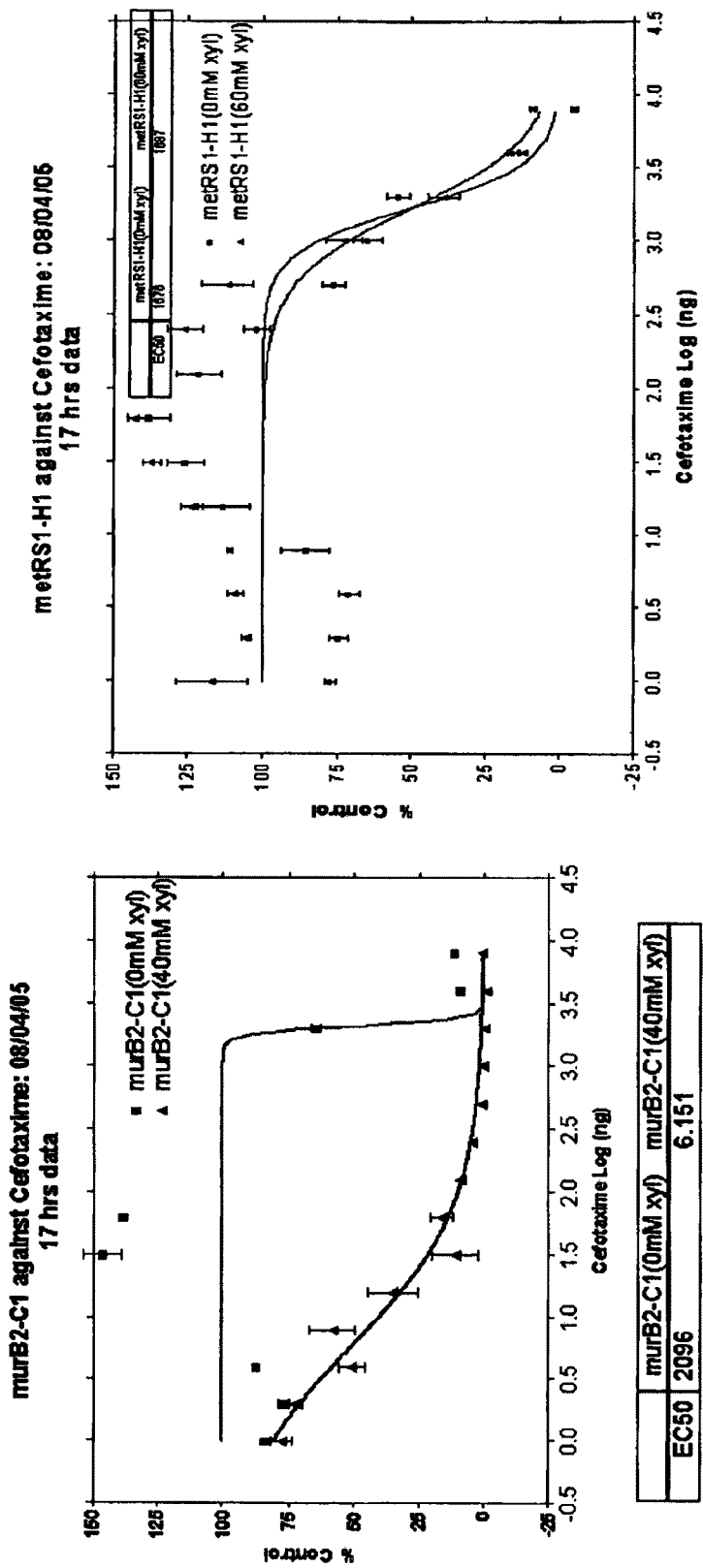
FIG. 2 shows the response of murB2 antisense clone to cefotaxime in the presence and absence of a subinhibitory concentration antisense inducer. Left panel: murB2 antisense clone. Upper line: no inducer. Lower line: +40 mM xylose. Right panel: metRS antisense clone. The ratio of the EC50+xylose/EC50 (−xylose) gives the 'IC50 shift'. In the example, the shift is computed to be (2096/6.1)=343.

Our interest in antisense has been in development of specific antisense strains of Bacillus anthracis for use in tracking the mechanism of action of new antibiotic candidates. One of our targets is MurB, the second step of peptidoglycan biosynthesis (FIG. 1). All bacterial pathogens require MurB; however, there are currently no antibiotics that act by inhibiting MurB.

Creation of a *B. anthracis* strain with inducible antisense to its functional murB gene (murB-2) resulted in a strain that was growth attenuated in the presence of inducer. The selected strains were determined to have antisense inserts that corresponded to various portions of the murB gene. The strains were then characterized in terms of the inducer-dependence of their growth attenuation and their sensitivity to a panel of antibiotics. Unexpectedly, some of the strains showed no difference in sensitivity to antibiotics. Thus, a crucial additional step in creating antisense-based tools for antibiotic discovery is the demonstration of increased sensitivity to certain antibiotics. We suspect that many of the antisense strains created by others are not useful in screening or in mode of action determination because they are not hypersensitive to inhibitors.

Of the validated murB antisense strains, unexpected and dramatic antisense synergism was observed for cell-wall inhibiting antibiotics. In four cases (cefepime, ceftriaxone, cefoxitin, or cefotaxime) murB antisense expression resulted in cells that were sensitive to 100-600 fold lower concentrations of the antibiotic relative to the cells in the un-induced condition (FIG. 3). Sensitivity to other cell wall-inhibiting antibiotics was increased but to lesser degrees. Sensitivity to antibiotics targeting other pathways such as protein synthesis, DNA synthesis, or RNA synthesis was not increased. The effect appears to be specific for genes in the peptidoglycan biosynthesis pathway, since antisense strains targeting other genes did not have this exceptional increase in sensitivity to any antibiotic tested.

FIG. 4 shows the sensitivity of a murA antisense strains to a panel of antibiotics. As was observed for murB antisense strains murA antisense expression resulted in cells that were many fold more sensitive to cell wall inhibiting antibiotics, but not to antibiotics targeting other pathways. Similar results have been obtained for antisense strains targeting the other genes in peptidoglycan biosynthesis.

While there is precedence for modest synergistic interactions between targets, the magnitude of the synergy between the MurB antisense strain and the cephalosporins is unprecedented. We have limited data on some weak MurB inhibitors in combination with cefotaxime that indicate synergism can be achieved using target inhibitors in place of antisense (FIG. 5). We have also shown that this phenomenon is not restricted to *B. anthracis*; murB antisense expression in *S. aureus* hypersensitizes cells to beta-lactam antibiotics (FIG. 6). Finally, we are in the process of characterizing this synergism in terms of 'Time-to-kill', an important parameter in antibiotic chemotherapy. We anticipate that combinations of cephalosporins with MurB inhibition will result in a shorter time to a bactericidal effect relative to the time for a bactericidal result of the cephalosporin by itself.

We further anticipate MurB inhibition will re-sensitize methicillin-resistant bacteria to methicillins and other penicillins otherwise ineffective at treating such infections.

With this observation in *B. anthracis* concerning MurB and cephalosporins, we anticipate other combinations of antibiotics and gene targets that can be discovered with this methodology. We anticipate these observations could translate to other important pathogens, especially *S. aureus*. FIG. 6 shows the increase in potency of cefoxitin and dicloxacillin on a strain of *S. aureus* engineered with inducible antisense to murB. The sensitivity of the *S. aureus* strain to a panel of antibiotics increased in the presence of inducer for beta-lactam antibiotics, but not antibiotics for other modes of action.

We also anticipate the ability to uncover other unexpected synergistic pairs of antibiotics and genes. These pairs could enable the discovery of target sites for the development of synergists for other antibiotics. Antisense in other organisms, including fungi and mammalian cells, could be exploited in a similar fashion for the discovery of synergistic target sites and ultimately synergistic compounds to enhance effectiveness of many classes of drugs, including anti-cancer drugs, psychotropic drugs, etc.

Therefore, it would be useful to be able to determine the potential for synergistic interactions between any given antibiotic and inhibitors of any specific target. Such a determination would allow construction of a screen for chemical compounds that would increase the potency of the given antibiotic. Inducible antisense could be the basis of a system for determining targets for synergist discovery and development. This use of antisense contrasts with its use in discovering gene essentiality; whereas the use of antisense to discover gene essentiality has been described by others, this use of antisense could result in detection of either essential genes or genes that are not essential but limit the potency of antibiotics in some way.

The use of synergistic combinations of drugs could have many advantages over conventional single compound chemotherapy, including lowered side-effects of drugs due to lower doses used or shorter time of chemotherapy; more rapid cure of infection, thus shortening hospital stays; increasing spectrum of pathogens controlled; decreasing incidence of development of resistance to antibiotics.

The importance of the antisense tool for determining genes of interest for antibiotic synergist discovery is that it provides an empirical method for developing novel screens without specific knowledge of the mechanism of antibiotic action, and without the use of a specific compound for the synergistic target. This use of antisense can uncover unexpected relationships between genes and antibiotic susceptibility for any given pathogen. FIG. 7 shows a process flow for the discovery of synergistic targets for antibiotics.

We have discovered synergistic interactions between MurB and beta-lactam antibiotics. This discovery anticipates the development of combinations of MurB inhibitors and beta-lactams that can enhance antiinfectives chemotherapy by reducing the dosage of the therapeutics, decreasing the time of treatment, or increasing the spectrum of pathogen control.

We have developed a general method for discovering synergistic targets for any given antibiotic using inducible antisense for a particular gene and comparing the antibiotic sensitivity of the organism in the presence and absence of inducer.

We anticipate the general use of antisense to enable discovery of targets synergistic with drugs thereby increasing drug efficacy. This use could extend to antiviral, antifungals, antiparsitics, antineoplastics, pesticides, herbicides, and other biological systems addressed by chemotherapy.

EXAMPLES

The following examples are meant to illustrate, and not to limit, the invention.

The following is an illustrative example for a method of the invention:

1) A gene or genes of interest (e.g., an operon) is PCR amplified using genomic DNA as a template. Care is taken to include about 200 bp on either end of the gene(s) to be surveyed.

2) That PCR fragment is fragmented by sonication; resulting fragments are blunt ended, size selected to be no bigger than about 350-400 bp, and then cloned into a polylinker immediately downstream of the inducible promoter in our expression plasmid, pBAX-2. Creation of this library is done typically in *E. coli*.

3) The DNA of the library is then transformed into the organism from which the gene of interest originated, e.g., *Bacillus anthracis* or *Staphylococcus aureus*. Individual colonies are collected by picking and cultured in 96 well culture dishes in growth medium that selects for presence of the plasmid.

4) After the cells have grown, they are replica plated (e.g., using a pin tool) onto a solid version of the original growth medium, either with or without the inducing compound xylose.

5) These replica platings are grown overnight and then compared as a plus and minus xylose pair; those colonies that show marked growth sensitivity only on the xylose plate are selected from the non-xylose plate for further study.

6) The fragment inserts in the pBAX-2 plasmids of the xylose growth sensitive strains are analyzed by DNA sequencing. This identifies where in the PCR-amplified gene of interest the fragment comes from, and also establishes if it is in the sense or antisense orientation relative to both the gene of interest and to the inducible promoter.

7) The relative number of senses and antisenses are logged. We've found that if the gene is essential, we will get predominantly antisense-oriented fragments in the xylose growth sensitive strain pool. If the gene is non-essential, we tend to see either no growth sensitives in equivalent number of colonies screened, or we see a more equal number of antisenses and senses. Please note that if you randomly select transformants before you apply the xylose screen, you will find that the antisense to sense numbers that you get remain about equal.

8) Select a number of the antisense clones for further analysis. These are selected for their relative position in the gene of interest (our current ability to analyze mRNA levels restricts us to more 3' fragments) and for their relative size. Often, the larger that the fragments are, the more likely they are to cause non-specific growth sensitivity.

9) Two studies are then done on these antisense clones. Measure the endogenous levels of transcript from the gene of interest in response to induction of expression of the antisense fragment. Specific degradation or reduction in message corresponding to the gene of interest and not to that of control genes is an indication that the antisense is working as a specific post-transcriptional inhibitor of gene of interest expression.

10) Another assay is to measure a specific phenotype change other than generic growth effects in response to induction of expression of the antisense fragment. In the case of our DHFR antisense, the test was to see if the antisense could cause thymidine auxotrophy. Biosynthesis of thymidine takes up the bulk of tetrahydrofolate that is synthesized by DHFR and auxotrophy is a classic effect of DHFR mutations. Another thing to do is to measure hypersensitivity to inhibitor compounds due to induction of antisense that are specific for the cellular product of the gene of interest, such as a specific antibiotic. Antisense should not cause hypersensitivity to inhibitors or antibiotics that are not specific to the gene or interest or are specific to unrelated cellular targets.

Although the invention has been described with reference to the above examples, it will be understood that modifications and variations are encompassed within the spirit and scope of the invention. Accordingly, the invention is limited only by the following claims.

The invention claimed is:

1. A method for treating bacterial infections in a subject or animal comprising administering to a subject or animal in need thereof, an antibacterially effective combination of a cephalosporin and an inhibitor of MurB;
   wherein a fractional inhibitory concentration index (FICI) of the combination is ≦0.5.

2. The method of claim 1, wherein the FICI is <0.2.

3. The method of claim 2, wherein the cephalosporin is ceftazidime, cefepime, ceftriaxone or cefotaxime.

4. The method of claim 1, wherein the cephalosporin is selected from the group consisting of cephalothin, cefazolin, cefalexin, cefuroxime, cefamandole, cefoxitin, cefaclor, cefaperazone, ceftazidime, ceftriaxone, cefepime, and cefotaxime.

5. The method of claim 4, wherein the cephalosporin is ceftazidime, cefepime, ceftriaxone or cefotaxime.

6. A method for treating bacterial infections in a subject comprising administering to a subject in need thereof, an antibacterially effective combination of a cephalosporin and a dihydropyrrolone inhibitor of a bacterial MurB enzyme.

7. The method of claim 6, wherein the cephalosporin is selected from the group consisting of cephalothin, cefazolin, cefalexin, cefuroxime, cefamandole, cefoxitin, cefaclor, cefaperazone, ceftazidime, ceftriaxone, and cefotaxime.

8. The method of claim 7, wherein the cephalosporin is ceftazidime, cefepime, ceftriaxone or cefotaxime.

9. The method of claim 1 wherein the inhibitor of MurB is an inhibitor of *B. anthracis* MurB or *S. aureus* MurB.

10. The method of claim 2 wherein the cephalosporin is selected from the group consisting of cephalothin, cefazolin, cefalexin, cefuroxime, cefamandole, cefoxitin, cefaclor, cefaperazone, ceftazidime, ceftriaxone, cefepime, and cefotaxime.

* * * * *

SEQUENCE LISTING

<160> NUMBER OF SEQ ID NOS: 15

<210> SEQ ID NO 1
<211> LENGTH: 113
<212> TYPE: DNA
<213> ORGANISM: Bacillus anthracis Ba-murB2-C1

<400> SEQUENCE: 1

```
ccgccaactg aacctggaat accacaagcg aactcaagac ccgttaagtt atggtctaac      60
gcaatacgtg atacgtcaat aattgctgca ccgcactgtg ctacaattgt cgt            113
```

<210> SEQ ID NO 2
<211> LENGTH: 124
<212> TYPE: DNA
<213> ORGANISM: Bacillus anthracis Ba-murB2-H1

<400> SEQUENCE: 2

```
ctcttcaact gttttttgta cgaagtgaat taaatcgatg taatcttgtg ctgttccgtt      60
atcaacattt accataaatc cagcgtgttt taaagaaacg gatcgaatgt cattattaaa    120
gacg                                                                  124
```

<210> SEQ ID NO 3
<211> LENGTH: 174
<212> TYPE: DNA
<213> ORGANISM: Bacillus anthracis Ba-murB2-D1

<400> SEQUENCE: 3

```
tgcattcata taatgctc cgccaactga acctggaata ccacaagcga actcaagacc       60
```

| cgttaagtta tggtctaacg caatacgtga tacgtcaata attgctgcac cgcactgtgc | 120 |
| tacaattgtc gttcctgtta cagtaacacc tgtaatatga attaaactta ctgt | 174 |

<210> SEQ ID NO 4
<211> LENGTH: 145
<212> TYPE: DNA
<213> ORGANISM: Bacillus anthracis Ba-murB2-D2

<400> SEQUENCE: 4

| aagttatggt ctaacgcaat acgtgatacg tcaataattg ctgcaccgca ctgtgctaca | 60 |
| attgtcgttc ctgttacagt aacacctgta atatgaatta aacttactgt aatcccgcga | 120 |
| attccaccgt ctttaataat gacat | 145 |

<210> SEQ ID NO 5
<211> LENGTH: 96
<212> TYPE: DNA
<213> ORGANISM: Bacillus anthracis Ba-metRS1-H1

<400> SEQUENCE: 5

| aatataactg gatctactac atttcctttt gacttactca tctttccatc cttcattaaa | 60 |
| atccaaccgt gagcaaagac ttttttcgga agaggt | 96 |

<210> SEQ ID NO 6
<211> LENGTH: 107
<212> TYPE: DNA
<213> ORGANISM: Bacillus anthracis Ba-metRS1-H2

<400> SEQUENCE: 6

| aacttatctg cctttttttac aggttcagca gatagtactt cagctacacg caattctact | 60 |
| ttaaagaaat catcaattgt aatttcttct gccttcggtc cttcttc | 107 |

<210> SEQ ID NO 7
<211> LENGTH: 103
<212> TYPE: DNA
<213> ORGANISM: Bacillus anthracis Ba-metRS1-H6

<400> SEQUENCE: 7

| atccttcatt aaaatccaac cgtgagcaaa gactttttc ggaagaggta aatctaatgc | 60 |
| cattaaaatg attggccaat aaattgtatg gaaacgaacg att | 103 |

<210> SEQ ID NO 8
<211> LENGTH: 93
<212> TYPE: DNA
<213> ORGANISM: Bacillus anthracis Ba-metRS1-E4

<400> SEQUENCE: 8

| ggttgtcctt tttctacttt tgttccagct ggaatacagc cgattgtaga taggcttccc | 60 |
| caagatgtat gtgcttcatc agtaaggcca agc | 93 |

<210> SEQ ID NO 9
<211> LENGTH: 99
<212> TYPE: DNA
<213> ORGANISM: Bacillus anthracis Ba-uppS-UG9

<400> SEQUENCE: 9

| tttaacgcga aattaagaat taatcccgta ttctctttcg tttcttccat ggccttctcc | 60 |
| atcgctctgc gtgtatgcgt aggaagacga tcttgttgc | 99 |

```
<210> SEQ ID NO 10
<211> LENGTH: 51
<212> TYPE: DNA
<213> ORGANISM: Bacillus anthracis Ba-uppS-UA3

<400> SEQUENCE: 10
cctctctttc tacacgcctc cgaatctgcg ccctctatgt tgaaagtctg t        51

<210> SEQ ID NO 11
<211> LENGTH: 103
<212> TYPE: DNA
<213> ORGANISM: Bacillus anthracis Ba-dfrA-2G1

<400> SEQUENCE: 11
ccaggcagtg gtctaccaat cgcttcatag tttttcttc ccataataag cgggtgaccc    60
atcgttgttt tctttacata ctgcaattca ctcggtaaac gcc                   103

<210> SEQ ID NO 12
<211> LENGTH: 107
<212> TYPE: DNA
<213> ORGANISM: Bacillus anthracis Ba-dfrA-2G6

<400> SEQUENCE: 12
caggcagtgg tctaccaatc gcttcatagt tttttcttcc cataataagc gggtgaccca    60
tcgttgtttt ctttacatac tgcaattcac tcggtaaacg ccaaggt                  107

<210> SEQ ID NO 13
<211> LENGTH: 198
<212> TYPE: DNA
<213> ORGANISM: Staphylococcus aureus Sa-murB-E9

<400> SEQUENCE: 13
ccaccttcac ggataataat atttgagcca tttcctaaat atgtaacagg aatctcattt     60
tgataggcat atttaacaac tgcttgtact tcttcatttt tagtaggggt aatgtaaaag   120
tcggcattac cacctgtttt agtataagtg tatcgtttta aggttcatc aactttaatt    180 ttttcatttg ggataagt                                                 198

<210> SEQ ID NO 14
<211> LENGTH: 169
<212> TYPE: DNA
<213> ORGANISM: Staphylococcus aureus Sa-murB-F7

<400> SEQUENCE: 14
cttgcaaatt agaatcttgt atcaatttac ctgcaaaatg accaggcggt ctttggaata     60
cactaccaca tgaaggatac tctaaaggtt gtttagattc tctacgttct gttaaatcat   120 ccatttagc ttgtatttca gtcattttac caggagctaa agtaaatgc                169

<210> SEQ ID NO 15
<211> LENGTH: 146
<212> TYPE: DNA
<213> ORGANISM: Staphylococcus aureus Sa-murB-B9

<400> SEQUENCE: 15
accaattgaa cctggaatac cacatgcaaa ttcaaggcca gtaagtgcgt aatcacgagc     60
aacacgtgag acatcaataa ttgcagcgcc gctaccggct attatcgcat catcagatac   120
ttcgatatga tctagtgata ataaac                                         146
```